United States Patent [19]

Pitchai et al.

[11] Patent Number: 5,686,380
[45] Date of Patent: Nov. 11, 1997

[54] VAPOR PHASE OXIDATION OF PROPYLENE TO PROPYLENE OXIDE

[75] Inventors: Rangasamy Pitchai, West Chester; Andrew P. Kahn, Lafayette Hill; Anne M. Gaffney, West Chester, all of Pa.

[73] Assignee: ARCO Chemical Technology, L.P., Greenville, Del.

[21] Appl. No.: 741,854

[22] Filed: Oct. 28, 1996

Related U.S. Application Data

[62] Division of Ser. No. 595,007, Jan. 31, 1996, Pat. No. 5,625,084.

[51] Int. Cl.$^6$ ............................................. B01J 23/50
[52] U.S. Cl. ............................................. 502/347; 549/536
[58] Field of Search ............................... 502/347; 549/536

[56] References Cited

U.S. PATENT DOCUMENTS

| | | | |
|---|---|---|---|
| 2,825,701 | 3/1958 | Hermann et al. | 252/475 |
| 3,560,530 | 2/1971 | Stiles | 549/536 |
| 3,962,285 | 6/1976 | Cusumano | 549/536 |
| 4,808,738 | 2/1989 | Lauritzen | 549/536 |
| 4,820,675 | 4/1989 | Lauritzen | 502/216 |
| 5,364,826 | 11/1994 | Kemp | 502/315 |
| 5,387,751 | 2/1995 | Hayden et al. | 549/534 |
| 5,486,628 | 1/1996 | Kemp | 549/536 |

FOREIGN PATENT DOCUMENTS

| | | | |
|---|---|---|---|
| 1282772 | 4/1991 | Canada | 252/85 |
| 1286687 | 7/1991 | Canada | 260/371.5 |
| 1286688 | 7/1991 | Canada | 260/371.5 |
| 1286689 | 7/1991 | Canada | 260/371.5 |

*Primary Examiner*—C. Warren Ivy
*Assistant Examiner*—Lyman H. Smith
*Attorney, Agent, or Firm*—Stephen D. Harper

[57] ABSTRACT

Propylene is converted to propylene oxide in a vapor phase oxidation process employing a silver catalyst supported on an alkaline earth metal carbonate and containing both a potassium salt such as potassium nitrate and a molybdenum promoter. The potassium salt and the molybdenum promoter may be simultaneously supplied by the use of a potassium salt of a molybdenum oxyanion. The efficiency of the process is greatly enhanced through the simultaneous inclusion of carbon dioxide and an organic halide in the feedstream. The feedstream need not contain a nitrogen oxide species such as NO to attain high propylene oxide selectivity.

16 Claims, No Drawings

VAPOR PHASE OXIDATION OF PROPYLENE TO PROPYLENE OXIDE

This is a division of Ser. No. 08/595,007, filed Jan. 31, 1996 now U.S. Pat. No. 5,625,084.

FIELD OF THE INVENTION

This invention relates to a process for the direct oxidation of propylene to propylene oxide in the vapor phase using molecular oxygen and particular supported silver catalysts.

BACKGROUND OF THE INVENTION

The direct oxidation of ethylene to ethylene oxide by molecular oxygen is well-known and is, in fact, the method used currently for commercial production of ethylene oxide. The typical catalyst for such purpose contains metallic or ionic silver, optionally modified with various promoters and activators. Most such catalysts contain a porous, inert support or carrier upon which the silver and promoters are deposited. A review of the direct oxidation of ethylene in the presence of supported silver catalysts is provided by Sachtler et al. in *Catalyst Reviews: Science and Engineering.* 23 (1&2), 127–149 (1981).

It is also well-known, however, that the catalysts and reaction conditions which are best suited for ethylene oxide production do not give comparable selectivities in the direct oxidation of higher olefins such as propylene. The discovery of vapor phase direct oxidation processes capable of providing propylene oxide in higher selectivity than is presently attainable thus would be most desirable.

SUMMARY OF THE INVENTION

This invention provides a process for epoxidizing propylene comprising contacting at a temperature of 180° C. to 350° C.:

(i) a feedstream comprised of propylene, an oxygen-containing gas, an organic halide, carbon dioxide and, optionally a nitrogen oxide species with;

(ii) a supported silver catalyst comprising (a) an inert refractory solid support comprising an alkaline earth metal carbonate;

(b) a catalytically effective amount of silver;

(c) a promoting amount of a potassium salt comprising potassium cation and a nitrogen oxyanion or precursor thereof; and (d) a promoting amount of a molybdenum promoter.

In one particularly desirable embodiment of the invention, the potassium salt comprises potassium cation and an anion selected from the group consisting of nitrate, nitrite, and other anions capable of undergoing displacement or other chemical reaction to form nitrate and/or nitrite anions under epoxidation conditions.

In another embodiment of the invention, the supported silver catalyst comprises a potassium salt of a molybdenum oxyanion such as potassium molybdate or the like. Such salts are capable of functioning simultaneously as promoter components (c) and (d).

Surprisingly, it has been discovered that high propylene oxide selectivity may be attained even in the absence of any nitrogen oxide species such as NO in the feed stream.

To achieve the highest propylene oxide selectivities, it is critical to operate the process by contacting a feed stream with a supported silver catalyst at a temperature of 200° C. to 300° C., said feed stream being comprised of 2 to 50 volume percent propylene, 2 to 10 volume percent oxygen, 50 to 500 ppm of an alkyl chloride, and 5 to 25 volume percent carbon dioxide, and said supported silver catalyst comprising an alkaline earth metal carbonate selected from calcium carbonate, barium carbonate and strontium carbonate, 25 to 60 weight percent silver, 0.5 to 3 percent by weight, calculated as potassium cation, of potassium nitrate and 0.05 to 2.5 weight percent, calculated as Mo, of a molybdenum promoter derived from an oxyanion compound of molybdenum. Alternatively, a potassium salt comprised of potassium cation and molybdenum oxyanion can be utilized in place of the potassium nitrate and molybdenum promoter.

An important advantage of the invention is that it is highly selective and thus capable of furnishing propylene oxide in relatively high yield. Moreover, the process may be operated in a continuous manner over a long period of time without significant deterioration of catalyst activity.

DETAILED DESCRIPTION OF THE INVENTION

The present invention is directed to a process for the vapor phase oxidation of propylene to propylene oxide, i.e., an epoxidation process performed in the presence of an oxygen—containing gas and a particular class of supported silver catalysts.

The support material used in the present invention is selected from one of several carbonate-containing carrier materials. The carbonate employed is an inorganic carbonate having a cation which is an alkaline earth metal ion, particularly calcium, strontium, magnesium or barium with calcium, strontium and barium being most preferred. Such carbonates are capable of providing exceptionally high propylene oxide selectivities and have been found to be surprisingly superior to other support materials in this respect. Suitable carbonate supports are described, for example, in Canadian Patent No. 1,282,772. The carriers of the present invention may exist in various forms. In one embodiment, the carrier is one in which the carbonate is the predominate (i.e., at least 50% by weight) or, preferably, substantially the exclusive component of the support (i.e., the support consists essentially of one or more alkaline earth metal carbonates). In other embodiments of the invention, the inorganic support material is used in conjunction with a solid substrate, i.e., a subsupport or substructure composed of a more conventional support material, such as alumina (preferably, alpha-alumina). This latter type of support may employ the carbonate material coated on individual, relatively small particles of substructure or subsupport or on a larger unit such as a three-dimensional framework having a honeycomb-type of structure.

A granular form of the carbonate support material is preferred in the present invention, particularly when used as the exclusive or predominant component of the support. Commercially available carbonate materials suitable for use in the present invention may be obtained as powders which can be converted to the preferred granular form by conventional methods, including those described in Canadian Pat. No. 1,282,772. As described in greater detail below, the carbonate support may then be impregnated, or coated, with a solution containing a silver compound and thereafter reduced to elemental silver.

Alternatively, as described below, the powdered carbonate support material may be combined with an appropriate silver-containing solution, such as that used conventionally to impregnate solid supports to form a slurry or paste. This material may then be spread on a suitable surface and dried and calcined at an appropriate temperature, such as about 500° C. This results in a carbonate support with silver being supported thereon in its elemental state. The catalyst may then be impregnated with solutions of the potassium salt and/or the molybdenum promoter and thereafter dried. As an alternative, the potassium salt and/or molybdenum promoter may be dissolved in the same silver-containing impregnation solution used to form the coating paste or slurry with the carbonate material.

The carbonate support material, before or after incorporation of the silver, potassium salt, and/or molybdenum promoter, can be formed into shaped composites suitable for use in propylene oxide manufacture. The composites may be formed by any suitable technique. For instance, it is possible to form the composites by compressing the support materials into a mold having a desired configuration. The size of the particles may be selected to be appropriate for the formation of the composite and are often in the range of about 0.001 to about 5 millimeters in major dimension.

When coated catalysts, i.e., those catalysts in which the carbonate material is coated on a substructure are employed, a slurry of the carbonate material, in either powder or granular form, may be mixed with the particles of support material and thereafter dried. As with the predominant or exclusive carbonate support materials described above, the coated catalysts may also be prepared by using a solution of a silver compound or the silver compound, a potassium salt, and a molybdenum promoter or the silver compound and the potassium salt or the silver compound and the molybdenum promoter to form the slurry, followed by suitable drying and calcination.

The surface areas of the carbonate support materials generally range from 0.6 to about 14 m²/g, preferably from about 1.5 to about 10 m²/g. However, carbonate support materials having surface areas higher than 14 m²/g are also effective for the purposes of this invention. The surface area is measured by the conventional B. E. T. method using nitrogen or krypton described by Brunauer, Emmett and Teller in *J. Am. Chem. Soc.* 60, 309–16 (1938).

The carrier materials used in the present invention may generally be described as porous or microporous and typically have water pore volumes of about 0.05 to 0.80 cc/g.

The supported silver catalysts are typically used as individual particles of irregular shape and size. This is true both for the predominate or exclusive carbonate supports as well as the carbonate-coated supports. However, in some instances the supports, particularly the carbonate-coated supports, may have a particular shape and size and this is especially true of the subsupports used with the carbonates. Typically the subsupports are formed into aggregates or "pills" of a size and configuration to be usable in tubular reactors. These pills may be formed by conventional extrusion and firing techniques. The pills generally range in size from about 2 mm to about 15 mm, preferably about 3 mm to about 12 mm. The size is chosen to be consistent with the type of reactor employed. In general, in fixed bed reactor applications, sizes ranging from about 3 mm to about 10 mm have been found to be most suitable in the typical tubular reactors used in commerce. The shapes of the carrier aggregates useful for purposes of the present invention can vary widely and can be any of the forms conventionally used in the heterogeneous catalyst art.

It has been unexpectedly discovered that exceptionally high selectivity to the desired propylene oxide product is only obtainable by careful selection of composition of the supported silver catalyst. The catalyst must contain not only an alkaline earth metal carbonate support and silver but also a potassium salt as well as a molybdenum promoter or, alternatively, a potassium salt of a molybdenum oxyanion. The support may be present either as predominantly or exclusively the carbonate, designated herein as "carbonate-support". The corresponding catalysts which include such support are designated "carbonate-supported catalysts". When the carbonate is coated on or in the presence of a substrate or subsupport, the support is designated "carbonate-coated support" and when the support is used in a complete catalyst, the designation for the catalyst is a "carbonate-coated catalyst". As used herein, the term "coated" is not intended to imply that one substance necessarily forms a layer on or envelops a second substance but merely refers to the procedure involved in the preparation of such material.

The carbonate- and carbonate-coated supports may be prepared as indicated above or obtained commercially. The carbonate-supported catalyst of the present invention may be prepared by any known method of introducing silver and/or a potassium salt, such as potassium nitrate, in soluble form, and/or a molybdenum promoter, in soluble form, to a support. A preferred method of introducing silver to the carbonate support is by an impregnation process in which a solution of a soluble salt or complex of silver in an amount sufficient to deposit the desired weight of silver upon the carrier is dissolved in a suitable solvent or "complexing/solubilizing" agent. The solution may be used to impregnate the support or carrier by immersing the carrier in the silver-containing impregnating solution and forming a pasty mixture or slurry. The slurry is then dried and calcined by placing the mixture in an oven or furnace at about 100° to about 120° C. for 0.5 to 6 hours and then heating the mixture at a temperature of from about 250° to about 600° C. for another 1 to 6 hours. This procedure accomplishes drying of the carbonate/silver mixture, removes volatile components and reduces the silver present to its elemental form.

The required potassium salt may be introduced to the catalyst as an impregnation solution in a separate impregnation step. Again, this may be done by any known manner of impregnating a porous material. Conveniently, this may be carried out by placing the catalyst material in a container, evacuating the container and thereafter introducing the salt solution. Alternatively, the support may be sprayed or sprinkled with the impregnating solution. The excess solution may then be allowed to drain off or the solvent may be removed by evaporation under reduced pressure at a suitable temperature. The catalyst may then be dried at a moderate temperature (e.g., at 120° C.) in a oven for one-half to five hours. Such a procedure is known as a "sequential" or "consecutive" method of preparation. The carbonate-supported catalyst may also be prepared by a "simultaneous" or "coincidental" method of preparation. With this method, the potassium salt is included in the silver compound-containing solution used to impregnate the carbonate support.

The carbonate-coated catalysts are prepared by coating a suitable substructure or subsupport material, preferably alumina, and most preferably alpha alumina, with a carbonate-containing slurry. This may contain only the carbonate, in which case the carbonate-coated support is further treated as indicated above to produce a silver or a silver and potassium nitrate or nitrite carbonate-coated catalyst. Alternatively, a carbonate/silver compound slurry or a carbonate/silver compound/potassium salt slurry or a carbonate/silver compound/molybdenum promoter slurry or a carbonate/silver compound/potassium salt/molybdenum promoter slurry may be produced in a sequential or coincidental procedure. Thus, in a sequential procedure, particles or pills of a suitable subsupport material, such as alpha-alumina, are coated with a slurry of a carbonate material and a soluble salt or complex of silver dissolved in a complexing/solubilizing agent. The particles or pills are thereafter drained and calcined in an oven at a temperature of about 250 to about 600 degrees C. for about three minutes to about four hours, the duration of heating being inversely proportional to the temperature employed. The catalyst is then impregnated in the manner described above with a solution of potassium salt followed by a solution of molybdenum promoter, and then dried. The carbonate-coated supports may also be formed by a coincidental procedure in which a carbonate/silver compound/potassium salt/molybdenum promoter slurry is used to coat particles or pills of a suitable subsupport. After draining, the catalyst is dried at a temperature and for a duration indicated above for those carbonate-coated catalysts prepared by the sequential procedure. The particular silver salt or compound used to form the silver-containing impregnating solution in a solvent or a complexing/solubilizing agent is not particularly critical and any silver salt or compound generally known to the art which is both soluble in and does not react with the solvent or complexing/-solubitizing agent to form an unwanted product may be employed. Thus, the silver may be introduced to the solvent or complexing/solubilizing agent as an oxide or a salt, such as nitrate, carbonate, or carboxylate, for example, an acetate, propionate, butyrate, oxalate, malonate, malate, maleate, lactate, citrate, phthalate, generally the silver salts of higher fatty acids, and the like.

A large number of solvents or complexing/solubilizing agents may be suitably used to form the silver-containing impregnating solution. Besides adequately dissolving the silver or converting it to a soluble form, a suitable solvent or complexing/solubilizing agent should be capable of being readily removed in subsequent steps, either by a washing, volatilizing or oxidation procedure, or the like. The complexing/solubilizing agent, preferably, should also permit solution to provide silver in the finished catalyst to the extent of preferably about 25 to about 60 percent silver, based on the total weight of the catalyst. It is also generally preferred that the solvents or complexing/solubilizing agents be readily miscible with water since aqueous solutions may be conveniently employed. Among the materials found suitable as solvents or complexing/solubilizing agents for the preparation of the silver-containing solutions are alcohols, including glycols, such as ethylene glycol, amines (including alkanolamines and alkyldiamines) and carboxylic acids, such as lactic acid, as well as aqueous mixtures of such materials.

Typically, a silver-containing solution is prepared by dissolving silver in a suitable solvent or complexing/solubilizing agent such as, for example, a mixture of water, ethylenediamine, oxalic acid, silver oxide, and monoethanolamine. The solution is then mixed with support particles and drained. Thereafter the particles are suitably dried.

As indicated above, after impregnation, the silver-impregnated carrier particles are treated to convert the silver salt or complex to silver metal and thereby effect deposition of silver on the surface of the support. As used herein, the term "surface", as applied to the support, includes not only the external surfaces of the carrier but also the internal surfaces, that is, the surfaces defining the pores or internal portion of the support particles. This may be done by treating the impregnated particles with a reducing agent, such as hydrogen or hydrazine and/or by roasting, at an elevated temperature to decompose the silver compound and reduce the silver to its free metallic state. Certain solubilizing agents such as alkanolamines, alkyldiamines, and the like may also function as reducing agents.

An alternative method of obtaining a carbonate-supported silver catalyst suitable for use in the process of this invention once it has been modified with potassium salt and molybdenum promoter is by co-precipitation of silver carbonate and alkaline earth metal carbonate from the respective nitrates or other water-soluble salts as described in U.S. Pat. No. 2,825,701 (incorporated herein by reference in its entirety). For example, a silver-containing carbonate support may be prepared by preparing an aqueous solution containing a silver salt such as silver nitrate and an alkaline earth metal salt such as calcium nitrate, preferably at a molar ratio from 1:1 to 1:4, dropwise adding, while stirring, an alkali metal carbonate solution such as potassium carbonate in water to form a co-precipitate of silver carbonate and alkaline earth metal carbonate. The co-precipitate may thereafter be washed, dried, impregnated with molybdenum promoter and/or potassium salt, and/or treated with a reducing agent or by calcination or the like to reduce the silver to its free metallic state. The sequence of such additional steps may be varied as desired. The co-precipitate may be coated or deposited onto a different granular, porous refractory material, as described in the aforementioned patent.

Although at least a catalytically effective amount of silver must be present in the finished catalyst (meaning an amount that provides a measurable conversion of propylene to propylene oxide), the silver concentration preferably is from about 2 percent to 70 percent, by weight, based on the total weight of the catalyst. More preferably, the silver concentration ranges from about 25 to 60 percent, by weight.

It has been discovered that the presence of certain specific potassium salts in the supported silver catalyst significantly enhances the efficiency of said catalyst as a propylene epoxidation catalyst. The anion must be a nitrogen oxyanion (i.e., an anion or negative ion which contains both nitrogen and oxygen atoms) such as nitrate and nitrite or a precursor thereof (i.e., an anion capable of undergoing displacement or other chemical reaction and forming a nitrogen oxyanion under epoxidation or catalyst preparation conditions). Potassium nitrate ($KNO_3$) is the preferred potassium salt.

The efficiency-enhancing potassium salt may be introduced to the catalyst in any known manner. Thus, impregnation and deposition of silver and a potassium salt may be effected coincidentally or sequentially, as described above. The preferred method is a sequential impregnation of the support wherein initial introduction of the silver-containing solution is followed by drying of the silver-containing support and heating and/or chemical reduction of the silver. This support is then impregnated with a solution of the potassium salt. The aforedescribed sequential impregnation procedure, when a Mo promoter is present, advantageously yields a catalyst that breaks in more quickly and attains steady state within 1000 minutes on stream. As will be explained subsequently in more detail, it is also preferred to introduce the molybdenum promoter to the catalyst prior to impregnation with the potassium salt. Sequential impregnation is also desirable where the feed stream does not contain any NO or other nitrogen oxide species. In another desirable embodiment of the invention, however, the potassium salt and the molybdenum promoter are simultaneously introduced through the use of a potassium salt of a molybdenum oxyanion such as potassium molybdate.

In order to perform coincidental impregnation, the potassium salt must be soluble in the same solvent or complexing/ solubilizing liquid used with the silver impregnating solution. With the preferred sequential procedure in which the silver is added first, any solvent capable of dissolving the salt which will neither react with the silver nor leach it from the support is suitable. Aqueous solutions are generally preferred, but organic liquids, such as alcohols, may also be employed. Suitable procedures for effecting introduction of the potassium salt to the solid support are well known in the art.

The required potassium salt is added in an amount sufficient to provide an improvement in one or more of the catalytic properties (e.g., selectivity, activity, conversion, stability, yield) of the supported silver catalyst as compared to a catalyst not containing the potassium salt (herein referred to as "promoting amount"). The precise amount will vary depending upon such variables as the nitrogen oxide species and concentration thereof employed in the epoxidation procedure, the concentration of other components in the feed stream, the amount of silver contained in the catalyst, the surface area of the support, the process conditions, e.g., space velocity and temperature, and morphology of support. Generally, however, a suitable concentration range of the added potassium salt, calculated as cation, is about 0.15 to about 5 percent, preferably about 0.5 to about 3 percent, by weight, based on the total weight of the catalyst. Most preferably, the salt is added in an amount of about 1.5 to about 2.5 weight percent K.

It has been unexpectedly found that the addition of a promoting amount of molybdenum (i.e., an amount that works effectively to provide an improvement in one or more catalytic properties of a catalyst as compared to a catalyst not containing molybdenum) to a potassium salt-containing supported silver catalyst improves the propylene oxide selectivity of such catalyst. The extent of promotion observed using molybdenum significantly exceeds that obtained when transition metal compounds other than Mo compounds are introduced into the catalyst. The exact form of the promoter under epoxidation operating conditions is not known. The molybdenum promoter, it is believed, is not present on the catalyst in the elemental form since the promoter is applied to the catalyst in the form of ions, salts, compounds, and/or complexes and the reducing conditions generally used to reduce the silver to metallic silver are not usually sufficient to reduce the molybdenum to the elemental form.

It is thought that the promoter deposited on the support or present on the catalyst is in the compound form, most probably in the form of an oxygen-containing or oxidic compound. In a presently preferred embodiment, the promoter is applied to the catalyst in the oxyanionic form, i.e., in the form of an anion, or negative ion which contains oxygen. Examples of anions of molybdenum that can be suitably applied include molybdate, dimolybdate, paramolybdate, other iso- and hetero-polymolybdates, phosphomolybdate, and the like. The anions can be prepared by the reactive dissolution of various non-anionic materials such as the oxides such as $MoO_3$ etc., as well as other materials such as carbonates, sulfates, halides, oxyhalides, hydroxyhalides, hydroxides, sulfides, etc., of molybdenum. As mentioned previously, the use of potassium salts of molybdenum oxyanions (e.g., potassium molybdate) avoids the need to utilize different compounds to introduce the necessary potassium salt and molybdenum promoter.

The carrier is impregnated with molybdenum promoter ions, salt(s), compound(s) and/or complex(es). This may be done at the same time that the other components of the catalyst are added or before and/or later. Preferably the molybdenum promoter and silver are incorporated into the catalyst prior to the addition of the potassium salt.

The preferred amount of promoter compound present on or deposited on the support or catalyst ranges from about 0.05 to 2.5 weight percent Mo (measured as the element irrespective of the form in which the promoter is present) based on the total weight of the supported silver catalyst. The degree of benefit obtained within the above-defined limits will vary depending upon particular properties and characteristics, such as, for example, reaction conditions, catalyst preparative techniques, surface area and pore structure and surface chemical properties of the support utilized, silver content of the catalyst, and potassium content of the catalyst.

The presence of the indicated and claimed promoting amount of molybdenum in this specification and claims does not preclude the use of other activators, promoters, enhancers, stabilizers, improvers, and the like. However, the present invention has unexpectedly been found to be capable of operating at relatively high efficiency even in the absence of other promoters such as rhenium.

The promoter compounds, salts and/or complexes used in the preparation of the instant catalysts are molybdenum compounds, salts and/or complexes that can be solubilized in an appropriate solvent. Preferably, the solvent is a water-containing solvent. More preferably the solvent is the same solvent used to deposit the silver and potassium salt. Preferred promoter compounds are the oxyanionic compounds of molybdenum preferably the ammonium and alkali metal oxyanionates, such as potassium molybdate, cesium molybdate, rubidium molybdate, ammonium molybdate, lithium molybdate, sodium molybdate and the like.

Propylene and an oxygen-containing gas (i.e., a gas comprising molecular oxygen) are brought together in a reactor in the presence of the previously described catalyst under conditions effective to accomplish at least partial epoxidation of the propylene. Typical epoxidation conditions include temperatures within the reaction zone of the reactor on the order of about 180° to 350° C. (more preferably, 200° to 300° C.) and pressures from about 1 to about 30 atmospheres. Inlet pressures may be as low as 14 to 75 psig. To achieve satisfactorily high selectivity to epoxide, it is critical that the feed stream to the reactor contain carbon dioxide as well as an organic halide (described in more detail hereafter). A gaseous nitrogen oxide species (described in more detail hereafter), may optionally be supplied to the reaction zone within the reactor by introducing said species to the feedstream containing propylene (fresh and/or recycled) and molecular oxygen.

The feedstream must contain an organic halide, optionally, a halogenated hydrocarbon other than propylene such as a saturated halogenareal hydrocarbon. The feedstream additionally must contain carbon dioxide; the presence of carbon dioxide, contrary to the expectation of the prior art, has been found to substantially improve the selectivity to propylene oxide obtained in the present process.

Examples of nitrogen oxide species suitable for optional introduction in the feedstream include at least one of NO, $NO_2$, $N_2O_4$, $N_2O_3$ or any gaseous substance capable of forming one of the aforementioned gases, particularly NO and $NO_2$, under epoxidation conditions, and mixtures of one of the foregoing, particularly NO, with one or more of CO, $PH_3$, $SO_3$ and $SO_2$. NO is the most preferred nitrogen oxide species. It has unexpectedly been found, however, that inclusion of such nitrogen oxide species in the feedstream is not necessary, as high propylene oxide selectivity may be accomplished even without such additive, particularly in the embodiment where the catalyst is prepared by a sequential impregnation process (i.e., the Mo promoter and Ag are introduced prior to the potassium salt).

The amount of gaseous nitrogen oxide species present (if any) is not critical. The optimum amount is determined, in part, by the particular potassium salt used and the concentration thereof, and by other factors noted above which influence the optimum amount of potassium salt. Typically, a suitable concentration of the nitrogen oxide species for epoxidation of propylene, is about 0.1 to about 2,000 ppm, by volume, when $N_2$ is used as ballast. When NO is used in the epoxidation of propylene, the preferred concentration is about 5 to about 2,000 ppm, more preferably about 20 to 500 ppm, by volume, with an $N_2$ ballast. However, as explained previously, the nitrogen oxide species concentration may be essentially zero.

The "oxygen-containing gas" employed in the reaction may be defined as including pure molecular oxygen, atomic oxygen, any transient radical species derived from atomic or molecular oxygen capable of existence under epoxidation conditions, mixtures of another gaseous substance with at least one of the foregoing, and substances capable of forming one of the foregoing under epoxidation conditions. Such oxygen-containing gas is typically introduced to the reactor either as air, commercially pure oxygen or other substance which under epoxidation conditions both exists in a gaseous state and forms molecular oxygen.

The gaseous components which are supplied to the reaction zone, or that region of the reactor where reactants and catalyst are brought together under epoxidation conditions, are generally combined before being introduced to the reactor. If desired, however, such components may alternatively be introduced separately or in various combinations. The feed stream having the particular composition previously described thus may be formed prior to or at the time the individual components thereof enter the reaction zone. The reactors in which the process and catalyst of the present invention are employed may be of any type known to the art. A brief description of several of the reactor parameters which may be used in the present invention is presented below.

In addition to propylene and oxygen (and, optionally, a nitrogen oxide species), the feedstream also must contain a performance-enhancing organic halide (preferably, an alkyl halide). The organic halide is preferably a volatile compound, i.e., a substance which predominantly exists in gaseous form under the temperature and pressure conditions present in the reaction zone. The normal boiling point of the organic halide is most preferably less than about 100° C. at atmospheric pressure. Compounds containing from 1 to 10 carbon atoms are preferred. Most preferably, the alkyl halide is a chloride species. The term alkyl halide includes both saturated and unsaturated halides, such as ethylene dichloride, ethyl chloride, vinyl chloride, methyl chloride and methylene chloride. Preferably, ethyl chloride is employed as the organic halide. Mixtures of different organic halides may be employed. The amount of organic halide employed will vary depending upon a variety of factors, including the concentration of propylene being oxidized, the particular potassium salt and nitrogen oxide species and the concentrations thereof, as well as other factors noted above as influencing the optimum amount of potassium salt and nitrogen oxide species. However, a suitable range of concentration for the organic halide in the oxidation of propylene is typically about 0.1 to about 2,000 ppm, more preferably about 50 to 500 ppm by volume, of the feedstream. In addition, a hydrocarbon, particularly a saturated hydrocarbon, such as methane, propane, or ethane, may be included in the feedstream. The feedstream may also contain a ballast or diluent, such as nitrogen, or other inert gas, particularly when air is used as the oxygen-containing gas. Varying amounts of water vapor may also be present.

Carbon dioxide is the other essential component of the feedstream in the epoxidation process of this invention. The presence of carbon dioxide, within certain limits, has been found to provide surprising improvement in propylene oxide selectivity. Desirable enhancements in selectivity are generally observed using 1 to 30 volume % $CO_2$ in the feedstream, with 5 to 25 volume % $CO_2$ being preferred.

The components of the feedstream are most suitably present in the amounts shown in the following tables.

| Component | Volume in % (or ppm) for Propylene Oxidation |
|---|---|
| propylene | about 2 to about 50% |
| oxygen | about 2 to about 10% |
| organic halide | about 0.1 to about 2,000 ppm, more preferably, about 50 to 500 ppm |
| nitrogen oxide species | 0 to about 2,000 ppm |
| hydrocarbon other than propylene | 0 to about 5% |
| carbon dioxide | 1 to 30%, more preferably 5 to 25% |
| nitrogen or other ballast gas | remainder. |

Although the present invention can be used with any size and type of vapor phase epoxidation reactor, including both fixed bed and fluidized bed reactors known to the art, it is contemplated that the present invention will find most widespread application in standard fixed bed, multi-tubular reactors such as those now in use as ethylene oxide reactors. These generally include wall-cooled as well as adiabatic or non-wall-cooled reactors. Tube lengths may typically range from about 5 to about 60 feet but will frequently be in the range of from about 15 to about 45 feet. The tubes may have internal diameters from about 0.5 to about 2.5 inches and are expected to be typically from about 0.8 to about 1.5 inches. A plurality of tubes packed with catalyst arranged in parallel within a suitable shell may be employed. GHSV generally range from about 500 to about 10,000 $hr^{-1}$. Typically GHSV values range from about 800 to about 3,000 $hours^{-1}$ at pressures from about 1 to about 30 atmospheres, commonly about 1.1 to about 5 atmospheres. Contact times should be sufficient to convert 0.5 to 70%, preferably 5 to 30%, of the propylene.

EXAMPLES

A preferred method of preparing a supported silver catalyst suitable for use in the process of the invention is as follows:

Step I. Place a 16 oz. wide mouth jar containing a Teflon-coated stir bar on a stir plate. Add 41.12 g ethylenediamine to jar, followed by 40.80 g distilled water. Mix well, then slowly add 41.20 g oxalic acid and allow to dissolve completely. Slowly add 71.20 g silver (I) oxide and allow to dissolve completely. Add 14.40 g ethanolamine and 1.20 g molybdic acid, diammonium salt, and mix well. Add 15.0 g distilled water and 51.4 g calcium carbonate. Add 10 mixing stones, cap the jar and ball mill for 4 hours, dry at 100° C. for 1 hour, then calcine at 300° C. for 4 hours.

Step II. Grind the solids obtained in Step I to a powder. Add 160 ml distilled water to a 500 mL one-neck round bottom flask. Dissolve 6.2 g potassium nitrate in the water and then add 120 g of ground solids from Step I. Mix for 20 minutes on rotary evaporator, then apply vacuum and heat to 60° C. Continue rotary evaporation until contents of flask appear dry. Dry the resulting solids at 110° C. for 2 hours. The resulting catalyst may then be pelletized and sieved to 14×30 mesh.

Example 1

In accordance with the invention, a supported silver catalyst was prepared comprising a calcium carbonate support, 54% Ag, 2%K (added as potassium nitrate), and 0.5% Mo (added as molybdic acid, diammonium salt). The supported silver catalyst (2 cc) was loaded in a tubular reactor and tested under the following run conditions: 10% propylene, 5% oxygen, 200 ppm ethyl chloride, 75 ppm nitric oxide, 10% carbon dioxide, and balance nitrogen, GHSV=1200 hr$^{-1}$, 30 psig total pressure, 245° C. Propylene conversion of 3.2% with 58–59% selectivity to propylene oxide were obtained.

Example 2

Example 1 was repeated, with the exception that the concentration of propylene was decreased to 5%, the concentration of carbon dioxide was increased to 20%, and the temperature was lowered to 240° C. Propylene conversion of 4.5% and 59–61% selectivity to propylene oxide were obtained.

Comparative Examples 3–4

These examples demonstrate the deleterious effect of omitting the molybdenum promoter from the supported silver catalyst. A catalyst was prepared comprising a calcium carbonate support, 43% Ag and 1.7% K (added as potassium nitrate). The catalyst (2 cc) was then loaded in a tubular reactor and tested under the following run conditions: 10% propylene, 5% oxygen, 50 ppm ethyl chloride, 200 ppm nitric oxide, and balance nitrogen, GHSV=1200 hr$^{-1}$, 30 psig total pressure, 250° C. Propylene conversion was 11% with only 33% selectivity to propylene oxide.

A second supported silver catalyst was prepared comprising a calcium carbonate support, 54% Ag, 2% K (added as potassium nitrate), and 0.5% Mo (added as molybdic acid, diammonium salt). The catalyst was then tested under the run conditions described above for the Mo-free catalyst. Propylene conversion was 11.2% with selectivity to propylene oxide of 39.5%. The additional of even small amounts of molybdenum to the catalyst thus clearly increased the epoxide selectivity to a significant extent under comparable testing conditions. Further improvements in selectivity are obtainable by addition of carbon dioxide to the reactor feed mixture in accordance with the invention.

Comparative Example 5

A supported silver catalyst (2 cc) comprised of a calcium carbonate support, 52% Ag and 2.1% K (added as KNO$_3$), but no molybdenum, was tested under conditions identical to these utilized in Example 1. Propylene conversion was 5.1%; propylene oxide selectivity was 50–52% (significantly lower than had been observed in Example 1 using a molybdenum-containing supported silver catalyst).

Comparative Example 6

A supported silver catalyst containing potassium molybdate was prepared as follows. Ethylene diamine (5.14 g), distilled water (5.17 g), oxalic acid dihydrate (5.15 g), silver(1) oxide (8.94 g), ethanolamine (1.87 g), potassium molybdate (0.779 g) in distilled water (1.88 g), and calcium carbonate (6.45 g) were combined in a 4 oz. jar containing 5 ceramic stones. The jar was sealed and placed on a ball mill for 4 hours. The resulting mixture was then heated at 110° C. for 1 hour; the temperature was thereafter increased at 10° C./min. to a maximum of 300° C. and held at 300° C. for 3 hours. The solids thus obtained were ground to a powder, pelletized, and sieved to 14×30 mesh. The resulting supported catalyst contained 51 weight % Ag, 1.6 weight % K, and 1.8 weight % Mo.

The above-described catalyst was loaded in a tubular reactor and tested under the following conditions: 10% propylene, 5% oxygen, 50 ppm ethyl chloride, 200 ppm nitric oxide, balance nitrogen; GHSV=1200 hr$^{-1}$; 30 psig total pressure; 250° C. Propylene conversion was 13% with 40% selectivity to propylene oxide. Further improvement in PO selectivity is expected with the incorporation of 1 to 30 volume percent carbon dioxide in the feed stream in accordance with the present invention.

Example 7

This example demonstrates that the presence of NO or other nitrogen oxide species in the feed stream is not necessary in order to achieve remarkably high propylene oxide selectivity. In accordance with the present invention, a supported silver catalyst was prepared comprising a calcium carbonate support, 53% Ag, 1.1% K (added as potassium nitrate), and 0.54% Mo (added as molybdic acid, diammonium salt). The catalyst (2 cc) was loaded into a tubular reactor and tested under the following conditions: 10 volume % propylene, 5 volume % oxygen, 200 ppm ethyl chloride, 10 volume % carbon dioxide, balance nitrogen; GHSV=1200 hr$^{-1}$, 30 psig total pressure, 245° C. Propylene conversion of 2.8% was achieved, with 58% selectivity to propylene oxide.

We claim:

1. A supported silver catalyst useful for vapor phase epoxidation of propylene comprising (a) a support material, at least 50% by weight of which is an alkaline earth metal carbonate, (b) 25 to 60 weight percent silver, (c) 0.5 to 3 weight percent, calculated as potassium cation, of a salt selected from potassium nitrate and potassium nitrite, and (d) 0.05 to 2.5 weight percent, calculated as Mo, of a molybdenum promoter.

2. The supported silver catalyst of claim 1 wherein the molybdenum promoter is derived from an oxyanionic compound of molybdenum.

3. The supported silver catalyst of claim 2 wherein the oxyanionic compound of molybdenum is an ammonium or alkali metal salt of molybdate, dimolybdate, paramolybdate, or phosphomolybdate.

4. The supported silver catalyst of claim 1 herein the salt is potassium nitrate.

5. The supported silver catalyst of claim 1 wherein the alkaline earth metal carbonate is calcium carbonate.

6. The supported silver catalyst of claim 1 prepared by a sequential impregnation procedure wherein the silver and the molybdenum promoter are impregnated on the support material prior to impregnation of the support material by the salt.

7. The supported silver catalyst of claim 1 comprising 1.5 to 2.5 weight percent, calculated as potassium cation, of the salt.

8. The supported silver catalyst of claim 1 wherein the support material consists essentially of the alkaline earth metal carbonate.

9. A supported silver catalyst useful for vapor phase epoxidation of propylene comprising (a) a support material, at least 50% by weight of which is an alkaline earth metal carbonate, (b) 25 to 60 weight percent silver, and (c) 0.5 to 3 percent by weight, calculated as potassium cation, of a molybdenum promoter derived from a potassium salt comprising potassium cation and a molybdenum oxyanion.

10. The supported silver catalyst of claim 9 wherein the molybdenum oxyanion is selected from the group consisting of molybdate, dimolybdate, and paramolybdate.

11. The supported silver catalyst of claim 9 wherein the potassium salt is potassium molybdate.

12. The supported silver catalyst of claim 9 wherein the alkaline earth metal carbonate is calcium carbonate.

13. The supported silver catalyst of claim 9 wherein the support material consists essentially of the alkaline earth metal carbonate.

14. A supported silver catalyst useful for vapor phase epoxidation of propylene comprising a support material consisting essentially of calcium carbonate, 25 to 60 weight percent silver, 1.5 to 2.5 weight percent, calculated as potassium cation, of potassium nitrate, and 0.05 to 2.5 weight percent, calculated as Mo, of a molybdenum promoter derived from an oxyanionic compound of molbdenum.

15. The supported silver catalyst of claim 14 wherein the oxyanionic compound of molybdenum is an ammonium or alkali metal salt of molybdate, dimolybdate, paramolybdate, or phosphomolybdate.

16. A supported silver catalyst useful for vapor phase epoxidation of propylene comprising (a) a support material consisting essentially of calcium carbonate, (b) 25 to 60 weight percent silver, and (c) 1.5 to 2.5 weight percent, calculated as potassium cation, of a molybdenum promoter derived from a potassium salt of molybdate, dimolybdate, or paramolybdate.

* * * * *